US008608929B2

(12) United States Patent
Marziali et al.

(10) Patent No.: US 8,608,929 B2
(45) Date of Patent: Dec. 17, 2013

(54) APPARATUS AND METHODS FOR CONCENTRATING AND SEPARATING PARTICLES SUCH AS MOLECULES

(75) Inventors: Andrea Marziali, North Vancouver (CA); David Broemeling, Vancouver (CA)

(73) Assignee: The University of British Columbia, Vancouver, BC ( * ) Notice: Subject to any disclaimer, the term of this patent is extended or adjusted under 35 U.S.C. 154(b) by 0 days.

(21) Appl. No.: 13/452,346

(22) Filed: Apr. 20, 2012

(65) Prior Publication Data

US 2012/0199481 A1    Aug. 9, 2012

Related U.S. Application Data

(63) Continuation of application No. 11/815,760, filed as application No. PCT/CA2006/000172 on Feb. 7, 2006, now Pat. No. 8,182,666.

(51) Int. Cl.
*G01N 27/26* (2006.01)

(52) U.S. Cl.
USPC ............ 204/457; 204/609; 204/458; 204/608

(58) Field of Classification Search
USPC ................ 204/155, 164, 450, 453, 456–462, 204/546–550, 554, 556, 600, 604–610, 204/643–645, 660–661; 205/698, 703, 205/792–793
See application file for complete search history.

(56) References Cited

U.S. PATENT DOCUMENTS

| | | |
|---|---|---|
| 4,148,703 A | 4/1979 | Trop et al. |
| 4,390,403 A | 6/1983 | Batchelder |
| 4,390,404 A | 6/1983 | Esho et al. |
| 4,732,656 A | 3/1988 | Hurd |
| 4,911,817 A | 3/1990 | Kindlmann |
| 5,084,157 A | 1/1992 | Clark et al. |
| 5,185,071 A | 2/1993 | Serwer |
| 5,286,434 A | 2/1994 | Slater |
| 5,384,022 A | 1/1995 | Rajasekaran |
| 5,609,743 A | 3/1997 | Sasagawa . |
| 5,938,904 A | 8/1999 | Bader |
| 6,036,831 A | 3/2000 | Bishop |
| 6,110,670 A | 8/2000 | Van Broeckhoven et al. |
| 6,146,511 A | 11/2000 | Slater |

(Continued)

FOREIGN PATENT DOCUMENTS

| | | |
|---|---|---|
| CA | 2552262 A1 | 11/2005 |
| CA | 2523089 A1 | 4/2006 |

(Continued)

OTHER PUBLICATIONS

Asbury, et al, "Trapping of DNA in nonuniform oscillating electric fields", Biophysical Journal, 1998, 74:1024-1030.

(Continued)

*Primary Examiner* — Susan D Leong
(74) *Attorney, Agent, or Firm* — Brown Rudnick LLP; Thomas C. Meyers

(57) ABSTRACT

Particles of interest, such as DNA molecules, are injected into a medium by applying a first field. Once in the medium the particles are concentrated by applying one or more fields that cause mobilities of the particles in the medium to vary in a manner that is correlated with motions of the particles. Particle injection and particle concentration may be performed concurrently or in alternation.

32 Claims, 6 Drawing Sheets

(56) References Cited

U.S. PATENT DOCUMENTS

| | | |
|---|---|---|
| 6,193,866 B1 | 2/2001 | Bader |
| 6,693,620 B1 | 2/2004 | Herb et al. |
| 6,824,664 B1 | 11/2004 | Austin et al. |
| 6,827,830 B1 | 12/2004 | Slater |
| 6,893,546 B2 | 5/2005 | Jullien |
| 7,175,747 B2 | 2/2007 | Bayerl et al. |
| 7,198,702 B1 | 4/2007 | Washizu |
| 7,371,533 B2 | 5/2008 | Slater |
| 7,427,343 B2 | 9/2008 | Han |
| 7,452,668 B2 | 11/2008 | Boles et al. |
| 2001/0045359 A1 | 11/2001 | Cheng et al. |
| 2002/0036139 A1 | 3/2002 | Becker et al. |
| 2002/0081280 A1 | 6/2002 | Curiel et al. |
| 2002/0119448 A1 | 8/2002 | Sorge et al. |
| 2002/0179445 A1 | 12/2002 | Alajoki et al. |
| 2003/0027178 A1 | 2/2003 | Vasmatzis et al. |
| 2003/0215855 A1 | 11/2003 | Dubrow et al. |
| 2005/0164402 A1 | 7/2005 | Belisle et al. |
| 2005/0247563 A1 | 11/2005 | Shuber et al. |
| 2005/0247564 A1 | 11/2005 | Volkel |
| 2007/0215472 A1 | 9/2007 | Slater |
| 2007/0218494 A1 | 9/2007 | Slater |
| 2008/0314751 A1 | 12/2008 | Bukshpan et al. |
| 2009/0120795 A1 | 5/2009 | Marziali |
| 2009/0139867 A1 | 6/2009 | Marziali et al. |
| 2009/0152116 A1 | 6/2009 | Boles et al. |
| 2011/0048950 A1 | 3/2011 | Marziali |

FOREIGN PATENT DOCUMENTS

| | | |
|---|---|---|
| CA | 2496294 A1 | 7/2006 |
| CA | 2641326 A1 | 10/2006 |
| EP | 0356187 A2 | 2/1990 |
| GB | 2249395 A | 5/1992 |
| JP | 2000-505545 A | 5/2000 |
| JP | 2001-165906 A | 6/2001 |
| JP | 2002-502020 A | 1/2002 |
| JP | 2003-062401 A | 3/2003 |
| JP | 2003-066004 A | 3/2003 |
| JP | 2003-513240 A | 4/2003 |
| JP | 2003-215099 A | 7/2003 |
| JP | 2003-247980 A | 9/2003 |
| WO | 9514923 A1 | 6/1995 |
| WO | 9727933 A1 | 8/1997 |
| WO | 9938874 A2 | 8/1999 |
| WO | 0131325 A1 | 5/2001 |
| WO | 0242500 A2 | 5/2002 |
| WO | 03019172 A2 | 3/2003 |
| WO | 2005072854 A1 | 8/2005 |
| WO | 2006063625 A1 | 6/2006 |
| WO | 2006081691 A1 | 8/2006 |
| WO | 2009094772 A1 | 8/2009 |
| WO | 2010051649 A1 | 5/2010 |
| WO | 2010/104798 A1 | 9/2010 |
| WO | 2010121381 A1 | 10/2010 |
| WO | 2013002616 A2 | 1/2013 |

OTHER PUBLICATIONS

Asbury, et al., "Trapping of DNA by dielectrophoresis", Electrophoresis, 2002, 23:2658-2666.

Astumian, R .Dean, et al., "Fluctuation driven ratchets: molecular motors", Physical Review Letters, 1994, 72 (11)1766-1769.

Bier, Martin, et al., "Biasing brownian motion in different directions in a d-state fluctuating potential and an application for the separation of small particles", Physical Review Letters, 1996, 76(22):4277-4280.

Carle, G.F., et al., "Electrophoretic separation of large DNA molecules by periodic inversion of the electric field", Science, 1986, 232(4746):65-68.

Chu, Gilbert. "Bag model for DNA migration during pulsed-field electrophoresis", Proc. Natl. Acad. Sci., 1991, 88:11071-11075.

Frumin, L.L., et al., "Nonlinear focusing of DNA macromolecules", Physical Review E—Statistical, Nonlinear and Soft Matter Physics, 2001, 64(2 Pat 1):021902-1-5.

Griess, Gary A., et al., "Cyclic capillary electrophoresis", Electrophoresis, 2002, 23:2610-2617.

Kopecka, K., et al., "Capillary electrophoresis sequencing of small ssDNA molecules versus the Ogston regime: fitting data and interpreting parameters", Electrophoresis, 2004, 25(14):2177-2185.

Magnasco, Marcelo, O., "Forced thermal ratchets", Physical Review Letters, 1993, 71(10):1477-1481.

Rousseau, J., et al., "Gel electrophoretic mobility of single-stranded DNA: The two reptation field-dependent factors", Electrophoresis, 2000, 21(8):1464-1470.

Slater, G.W., et al., "Recent developments in DNA electrophoretic separations", Electrophoresis, 1998, 19 (10):1525-1541.

Slater, G.W., et al., "Theory of DNA electrophoresis: a look at some current challenges", Electrophoresis, 2000, 21:3873-3887.

Slater, Gary W., et al., "The theory of DNA separation by capillary electrophoresis", Current Opinion in Biotechnology, 2003, 14:58-64.

Tessier, F. et al., "Strategies for the separation of polyelectrolytes based on non-linear dynamics and entropic ratchets in a simple microfluidic device", Applied Physics A. 2002, 75:285-291.

Turmel, C., et al., "Molecular detrapping and band narrowing with high frequency modulation of pulsed field electrophoresis", Nucleic Acids Res., 1990, 18(3):569-575.

Viovy, J.L., "Electrophoresis of DNA and other polyelectrolytes: Physical mechanisms", Reviews of Modern Physics, 2000, 72(3):813-872.

Marziali, A. et al., "Novel Electrophoresis Mechanism Based on Synchronous Alternating Drag Perturbation", Electrophoresis 2005, 26:82-89, published on-line Dec. 29, 2004 at URL www.3.interscience.wiley.com/cgi-bin/issue/109861245.

Frumin, L.L. et al., "Anomalous Size Dependence of the Non-Linear Mobility of DNA", PhysChemComm 2000, vol. 11, published Oct. 16, 2000.

Chacron, M.J. et al., "Particle Trapping and Self-Focusing in Temporally Asymmetric Ratchets with Strong Field Gradients", Physical Review E, Sep. 1997, 56(3):3446-3450.

Baba, Yoshinobu, "Capillary Affinity Gel Electrophoresis", Molecular Biotechnology, 1996, (9):1-11.

International Search Report for PCT/CA2012/050576, Feb. 28, 2013 3 pages.

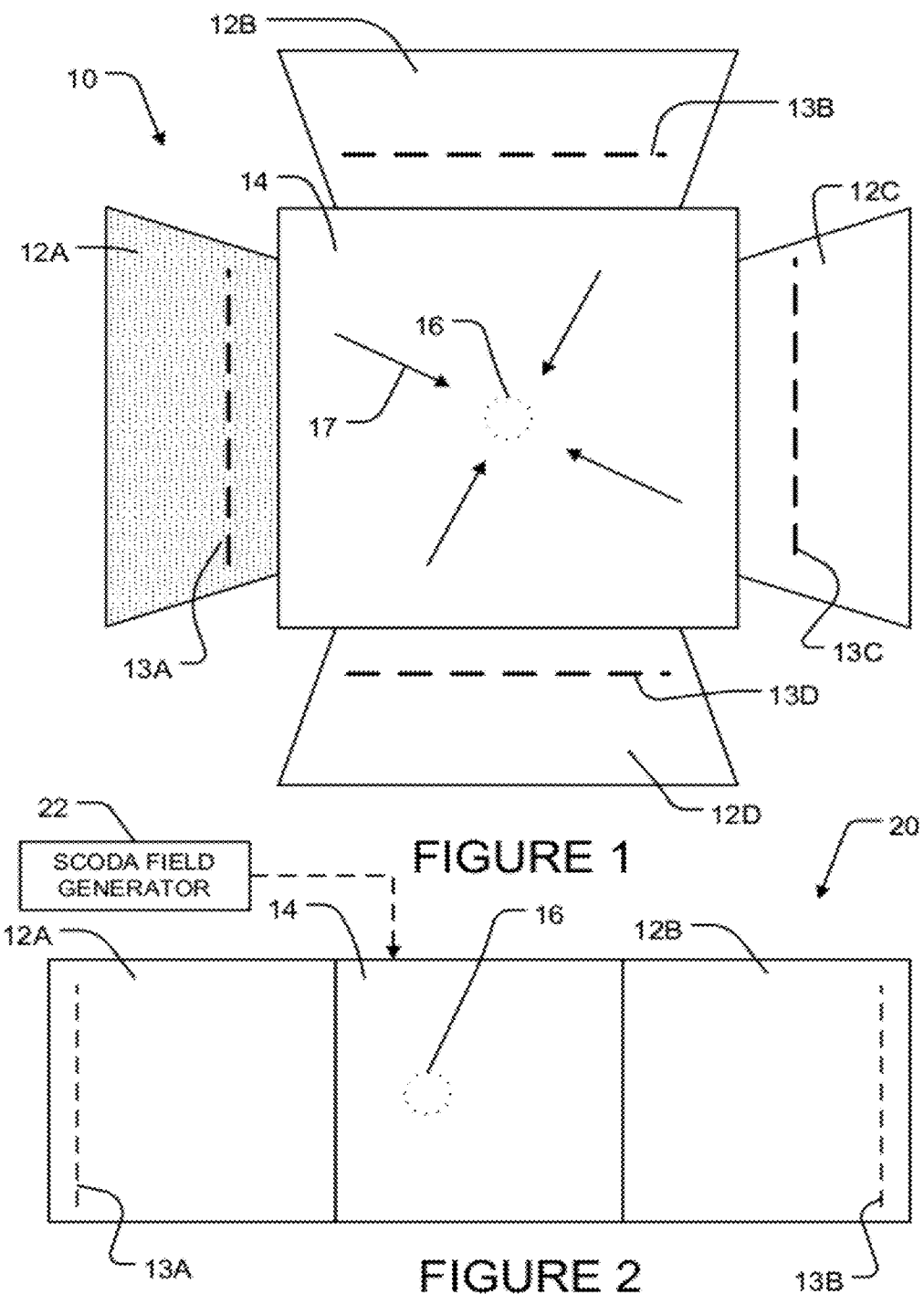

APPARATUS AND METHODS FOR CONCENTRATING AND SEPARATING PARTICLES SUCH AS MOLECULES

CROSS-REFERENCE TO RELATED APPLICATIONS

This application is a continuation of U.S. patent application Ser. No. 11/815,760 filed on 7 Aug. 2007, now U.S. Pat. No. 8,182,666 which is a 371 of PCT International Patent Application No. PCT/CA2006/000172 filed on 7 Feb. 2006, which claims priority from Canadian Patent Application No. 2,496,294 filed on 7 Feb. 2005, all entitled APPARATUS AND METHODS FOR CONCENTRATING AND SEPARATING PARTICLES SUCH AS MOLECULES and which are hereby incorporated herein by reference.

FIELD OF THE INVENTION

The invention provides methods and apparatus for guiding the motions of particles, such as molecules, for example, DNA, RNA, proteins and other biomolecules. The invention may be applied in systems for concentrating molecules and/or separating molecules of different types, lengths and/or physical or chemical characteristics. Some applications involve selectively trapping particles in a gel material that is subjected to continuous or pulsed electrokinetic injection of a sample.

BACKGROUND

There are many fields in which it is desirable to concentrate particles so that the particles can be studied. Consider for example the wide range of fields in which it may be desirable to collect molecules of DNA for study. Such fields include crime detection, medical studies, paleology, environmental studies and the like. The DNA of interest may be present initially in exceedingly low concentrations. There is a need for practical ways to concentrate particles, such as DNA.

SUMMARY OF THE INVENTION

This invention has a number of aspects. One aspect of the invention provides a method for concentrating selected particles. The particles may, for example, comprise DNA molecules, RNA molecules or denatured proteins. In specific embodiments of the invention the particles comprise DNA. The method comprises providing particles, including the selected particles, in a first region and applying a first field directed to move at least the selected particles from the first region into a second region. At least the second region is a region of a medium in which a mobility of the selected particles is dependent on an intensity of one or more second fields. When the selected particles are in the second region the method proceeds by concentrating the selected particles in a vicinity of a point in the second region by applying the second fields.

Another aspect of the invention provides a method for concentrating particles of interest. The method comprises driving the particles into a medium by applying a particle-injecting electric field across a boundary between the medium and a sample containing the particles of interest; and, applying scodaphoresis to the particles of interest in the medium to concentrate the particles of interest at a location in the medium.

Another aspect of the invention provides apparatus for concentrating particles of interest. The apparatus comprises: a buffer reservoir capable of receiving a sample; a medium in which particles of interest have a mobility that depends upon the intensity of applied fields; means for applying a first field to drive particles of interest from the buffer reservoir into the medium; and, means for applying one or more second fields to concentrate the particles of interest at a focal spot within the medium.

Further aspects of the invention and features of embodiments of the invention are described below.

DESCRIPTION OF THE FIGURES

The attached Figures are intended to aid in the visualization of potential embodiments of the technology, they should not be interpreted as limiting with respect to the scope of the invention described herein.

FIG. 1 is a schematic view of a SCODA setup having 4 large buffer reservoirs around 4 sides of a gel;

FIG. 2 is a schematic view of a gel cast with buffer reservoirs on two sides.

DESCRIPTION

Figure 3:
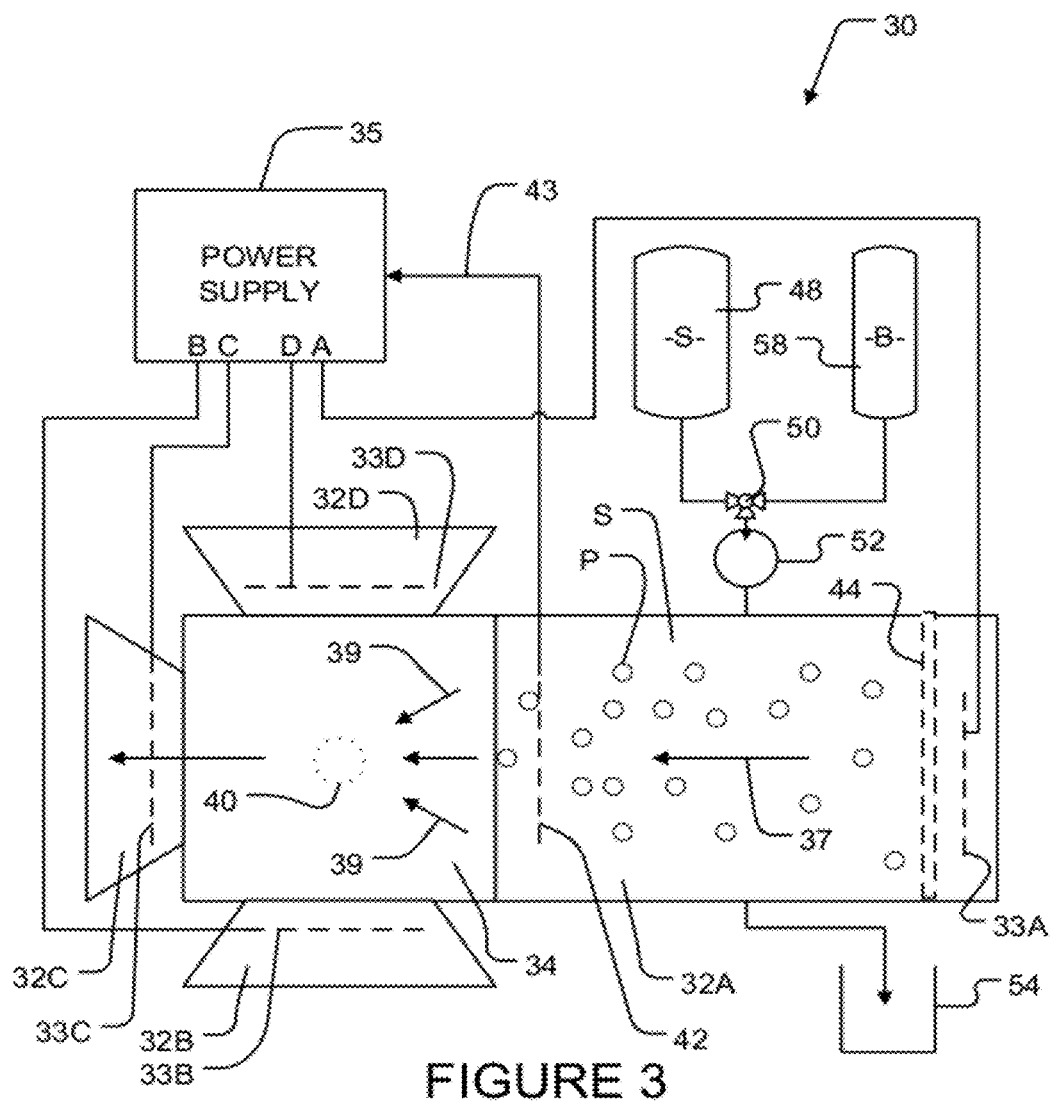
FIG. 3 shows apparatus for performing SCODA and electrokinetic injection from a sample reservoir.

SCODAphoresis (hereinafter referred to as SCODA) is described in U.S. patent application No. 60/540,352 filed 2 Feb. 2004, PCT patent application No. PCT/CA2005/000124 entitled "Scodaphoresis and Methods and Apparatus for Moving and Concentrating Particles" filed on Feb. 2, 2005; and Marziali, A.; et al., "*Novel electrophoresis mechanism based on synchronous alternating drag perturbation*", Electrophoresis 2005, 26, 82-89 all of which are hereby are incorporated herein by reference. Since SCODA is described in these published materials it is not described in detail herein.

SCODA is a process that can be used for concentrating particles (which may consist of or include certain molecules, such as DNA). SCODA can be used to concentrate the particles in the vicinity of a point in a region of a suitable material in which the particles have mobilities that vary in response to an applied field or combination of applied fields. Where the particles are electrically-charged molecules, such as DNA, the applied fields may comprise electric fields. The material may comprise a suitable gel such as an agarose gel, for example.

SCODA does not require electrodes to be present at the location where particles are concentrated. In one embodiment SCODA provides focusing and concentration of molecules based on the non-linear dependence of the particles' velocity on the strength of an applied electric field. This can also be stated as being based on the field dependence of the particles' mobility. The velocity, v of a particle in an electric field can be expressed as:

$$\vec{v}(t) = \mu(E) \cdot \vec{E} \quad (1)$$

where μ is the mobility of the particle and E is the magnitude of the applied electric field. In some media the mobility μ is reasonably approximated by:

$$\mu(E) = \mu_0 + kE \quad (2)$$

where $\mu_0$ and k are constants. In such media, the particle velocity varies non-linearly with the magnitude of the applied electric field.

Under the application of SCODA fields, molecules for which the value of k is large have a greater tendency to focus than particles with smaller values of k. In one embodiment of SCODA, a sample containing particles of interest mixed with other particles is introduced into a gel. The material of the gel and/or SCODA fields are selected so that the particles of interest have large values for k while other particles present in the gel have smaller values for k. When SCODA fields are applied, the particles of interest tend to be focused in a spot at a location determined by the SCODA fields. Molecules with low values for k remain distributed throughout the gel.

This effect is also impacted by the ability of the molecules to diffuse in the gel. The SCODA velocity toward the center of the gel is proportional to k and to the distance r from the location at which the molecules become concentrated. In an ideal case where the molecules of interest have mobilities given by Equation (2) it can be shown that:

$$|\vec{v}| = -\frac{kEE_q}{4}r \quad (3)$$

where v is the average velocity of the molecules in a direction of the focal point around which the molecules become concentrated, E is the magnitude of the SCODA electric field, and $E_q$ is the charge on the molecules.

The ability of molecules to focus (e.g. 1/radius of the focused spot) is proportional to:

$$\sqrt{\frac{k}{D}} \quad (4)$$

where D is the diffusion constant of the molecules in the gel (or other medium). Particles with a large value of this parameter tend to focus in the vicinity of a point in the gel under SCODA conditions, and are selectively concentrated relative to concentrations of other molecules with a smaller value of this parameter.

Particles may be injected into a region of a medium within which the particles can be concentrated by SCODA by providing the particles in an adjacent region and applying a field that causes the particles to move into the region of the SCODA medium. The adjacent region may be called a first region and the region of the SCODA medium may be called a second region. The field that causes the particles to move from the first region into the second region may be called a first field. The first field may comprise any field to which particles of interest respond by moving. Where the particles are electrically charged, the first field may comprise an electric field.

Depending upon the nature of the particles of interest, the first field may comprise any of:
  a magnetic field;
  an electric field;
  a flow field; or,
  some combination thereof.

In one embodiment, DC (Direct Current) electrophoresis is used to introduce particles from a sample into a SCODA medium such as a precast gel. After particles have been introduced into the gel, SCODA can be applied to concentrate selected particles at a location in the gel. DC electrophoresis may be applied to drive particles from a flowing sample into a SCODA medium.

The sample may comprise a liquid in which the particles are entrained. In some embodiments a liquid sample is introduced into a chamber adjacent to the SCODA medium and particles are driven from the chamber into the SCODA medium by electrophoresis until a desired quantity of particles are present in the SCODA medium or until the sample is depleted of particles. In other embodiments the sample is changed either continuously or intermittently and the first field is applied either continuously or intermittently to inject particles from the sample into the SCODA medium. Changing the sample may comprise intermittently removing some or all of the sample and replacing the removed sample with fresh sample. In some embodiments, changing the sample comprises allowing a liquid, which constitutes the sample, to flow through a chamber adjacent to the SCODA medium.

In cases where the sample is replenished, particles of interest that occur in the sample in exceedingly small concentrations can be collected at the focus in the SCODA medium over time. A very large concentration factor can be achieved in this manner.

Where the first field comprises a DC electrophoresis field, the field may be such that only certain charged species of interest are extracted from sample and introduced into the medium. For example, in some embodiments, DC electrophoresis is used to carry charged molecules which include nucleotide polymers, such as DNA, into the gel or other SCODA medium. Particles that are not charged or particles that have charges of the opposite polarity to the desired charged molecules are not moved into the SCODA medium.

It is not necessary that the magnitude of the first field be constant or even that the first field always have the same polarity. All that is required is that there is a net flow of particles of interest into the SCODA medium under the influence of the first field.

SCODA is performed by applying one or more SCODA fields within the SCODA medium. As described in PCT patent application No. PCT/CA2005/000124, for appropriate selection of SCODA fields, particles and SCODA media, the application of the SCODA fields causes selected particles within the SCODA medium to converge to a focal point so that the selected particles become concentrated in a vicinity of the focal point. The SCODA fields may be called "second fields". The second fields may co-exist with the first field in any of a number of ways including:

The first field is superposed on the second field(s) such that the first and second fields are applied simultaneously; or, The first field is interspersed in time with the second field(s) such that only the first field is applied for a first period of time, and only the second field(s) is applied for a second period of time. This pattern may be repeated at least until the selected molecules or other particles from the sample have been introduced into the SCODA medium; or, Some combination of these, for example, the first field may be applied during selected portions of a cycle of the second field(s) or the first field may be applied both during selected portions of a cycle of the second field (s) and also during periods when the second field(s) is not being applied.

The use of a DC field to inject particles into a SCODA medium permits:

Gel for use as a SCODA medium may be cast in relatively pure buffer, rather than in sample (which may be sufficiently contaminated to preclude satisfactory gel casting);

Only molecules of one charge species enter the gel in the first place, so neutral, and oppositely charged molecules are left behind and do not contaminate the gel;

Only the desired molecules with high values of $k/\mu_0$ are trapped. These can be extracted by shutting off the DC field, allowing the focus to move to the center, and performing any suitable extraction method.

The effective value for k for some molecules such as DNA can be made different for different sizes (e.g. lengths) of molecule by adjusting the frequency of the SCODA driving field(s).

Particles that have become concentrated in the vicinity of a point in the SCODA medium may be extracted in any suitable manner including: removing a portion of the gel or other SCODA medium that contains the concentrated particles; or causing the concentrated particles to move out of a plane of the SCODA medium by applying electric or other fields; or the like.

Any suitable combination of fields may be used to provide SCODA focusing of molecules. It is not necessary that the SCODA use electric fields. This invention can be applied to any system that employs SCODA in any of the embodiments described in the above referenced SCODA patent applications.

Example Operation of the Invention

FIG. 1 shows example apparatus 10 for performing concentration by SCODA. Apparatus 10 includes a sheet 14 of gel medium located amid buffer reservoirs 12A to 12D (collectively buffer reservoirs 12). One buffer reservoir is on each side of gel 14. Electrodes 13A to 13D are each immersed in a corresponding one of the buffer reservoirs. Electrodes 13A to 13D (collectively electrodes 13) are connected to different channels of a programmable power supply that applies potentials to electrodes 13 to provide a SCODA field in gel 14. Under the influence of SCODA fields, mobile particles in gel 14 (such as molecules) remain nearly stationary if they have values of $k \cong 0$. All appropriately-charged molecules with non-zero k move toward a central focus 16 as indicated by arrows 17. For example, SCODA fields may be provided that cause negatively-charged particles to move toward central focus 16 while positively-charged particles move away from central focus 16, or vice versa.

Particles may be introduced into gel 14 by introducing the particles into the buffer in one of buffer reservoirs 12 (for example, buffer reservoir 12A) and applying a potential difference between the corresponding electrode 13 and one or more other ones of electrodes 13 to create a first electric field directed to cause particles, which may be molecules in the buffer reservoir 12, to move toward gel 14. Typically the first electric field is created by establishing a potential difference between two electrodes that are on opposite sides of SCODA medium 14 (for example, between electrodes 13A and 13C). This DC field has a polarity selected so that charged molecules or other particles of interest will be injected from the buffer 12 into the SCODA gel 14. The DC field may be an applied electric field of the type commonly used in DC electrophoresis.

In buffer 12, the particles move toward gel 14 with a velocity proportional to their mobility in the buffer, $\mu_{BUF}$, until they enter gel 14. Within gel 14, the particles follow a combined motion with mobility $\mu_0$ (which will typically be different from $\mu_{BUF}$) with respect to the first field, and, while the second (SCODA) field(s) is applied, with an effective mobility proportional to k with respect to the second field(s).

Once in gel 14 (or other medium), particles having low values for k will behave as in DC electrophoresis, and will migrate through gel 14. If the first field is applied for long enough, such molecules may traverse completely across gel 14 until they escape into the buffer reservoir 12 opposed to the buffer reservoir 12 from which they originated.

Particles with high values of k will be focused by the SCODA field once they have entered gel 14 and will be trapped in gel 14 (as long as the first field—which may be a DC electric field—is not so strong as to overwhelm the SCODA velocity given to such particles). The location of the focus at which particles become concentrated will be shifted from the location of the focus in the absence of the first field. The amount of shift is based on the ratio of $\mu_0/k$ and on the relative amplitudes of the first and second fields. For some particles k may be frequency-dependent. In such cases the amount of shift may also depend upon the frequency of the second field(s).

The buffer reservoir 12 into which particles are introduced need not be large and could be a buffer-filled space between an electrode and medium in a typical SCODA apparatus like apparatus 10 of FIG. 1. If the particles are of a type that could be damaged by electrochemical reactions at the electrode then the particles should be introduced at a location such that the particles do not need to pass by the electrode before entering the medium. For example, the particles could be introduced into a region between the electrode and the medium. Providing a larger buffer reservoir and/or a buffer reservoir that permits fluid to be circulated permits extracting particles of interest from larger sample volumes and makes possible greater degrees of concentration.

FIG. 2 is a schematic view of apparatus 20 comprising a region of a gel 14 cast with buffer reservoirs 12A and 12B on two opposed sides. Apparatus 20 is similar to a conventional electrophoresis apparatus. A DC field is created by applying a potential difference between electrodes 13A and 13B. A sample containing molecules or other particles of interest is placed in one of the buffer reservoirs 12. Appropriate polarity of the DC field causes molecules of a desired charge to enter gel 14 from the sample. The molecules typically have mobilities $\mu_{BUF}$ in the buffer reservoir 12 that are significantly greater than their mobilities $\mu_0$ in gel 14. This causes molecules to initially stack at the edge of gel 14 and then separate into bands of different mobility. Typically, differently sized molecules travel in bands through the gel at different velocities. By applying SCODA fields when particles of interest are in gel 14, the particles of interest can be made to collect in the vicinity 16 of a focal point. Other particles pass through gel 14 into the opposing buffer reservoir 12. A mechanism 22 applies suitable SCODA fields within gel 14.

FIG. 3 shows apparatus 30 which combines features for efficiently performing electrophoretic injection of molecules from a sample into a medium and subjecting molecules in the medium to SCODA. Apparatus 30 is similar to apparatus 10 FIG. 1 except that one buffer reservoir 32A is made substantially longer than the other buffer reservoirs 32B through 32D to allow a significant volume of a sample S containing particles P to be injected. Each buffer reservoir is in electrical contact with a corresponding electrode 33. Electrode 33C is located at an end of buffer reservoir 32A so that buffer reservoir 32A and SCODA medium 34 lie between electrodes 33A and 33C.

Particles P can be driven into medium 34 by applying a potential difference between electrodes 33A and 33C with a power supply 35. The potential difference causes particles P to move into medium 34 as indicated by arrow 37.

Power supply 35 is also capable of applying time-varying potentials to electrodes 33 to cause SCODA fields within medium 34. The SCODA fields, when present, cause selected particles within medium 34 to converge toward the vicinity 40 of a focal point as indicated by arrows 39.

It is preferable to provide SCODA electric fields using electrodes that are located symmetrically relative to medium 34. Apparatus 30 has a sensing electrode 42 provided at a location that is symmetrical with respect to electrode 33C. If electrode 42 were used as a SCODA electrode then the sourcing or sinking of current at electrode 42 could damage particles P as they pass by electrode 42. Sensing electrode 42 provides a feedback signal 43 to power supply 35. Power supply 35 receives signal 43 at a high impedance input so that virtually no current is sourced or sinks at electrode 42.

Power supply 35 controls the potential applied to electrode 33A based upon feedback signal 43 to cause the potential at electrode 42 to track a desired SCODA waveform. This may be accomplished by providing a controller which uses a difference between the potential sensed at sensing electrode 42 and the desired SCODA potential as negative feedback. The potential at electrode 42 can be controlled at a desired value by appropriately regulating the potential applied to electrode 33A. Thus sensing electrode 42 in combination with the control in power supply 35 serves as a virtual SCODA electrode. This permits attainment of the proper SCODA field even though electrode 33A is displaced from its ideal position adjacent to medium 34.

In some cases providing a sensing electrode 42 closer to medium 34 and using a sensed voltage 43 to control the potential on a current-sourcing (or current-sinking) electrode farther from the medium (such as electrode 33A) can help to make the SCODA fields independent of the electrical conductivity of sample S. Electrical conductivity of different samples may vary due, for example, to variations in salinity between the samples.

Apparatus like that of FIG. 3 may be used to concentrate selected molecules that are present in sample S by applying particle-injecting and SCODA fields in alternation. For example, a DC field may be applied between electrodes 33A and 33C such that particles P such as charged molecules of interest move from sample reservoir 32A into medium 34 (this phase may be termed DC injection). DC injection is performed at least until molecules of interest in the buffer are significantly removed from the area around electrode 33A.

At the end of sample buffer 32A that adjoins medium 34 molecules are injected into medium 34. After an appropriate time, the DC field is shut off, and the SCODA field is turned on. Preferably the SCODA field is not turned on until after the molecules of interest have been driven far enough from electrode 33A that any reverse DC field temporarily applied during SCODA operation does not drive molecules into electrode 33A where they may be chemically altered. To ensure this, the amount of time that the DC field and SCODA fields are applied for should obey:

$$T_{INJ}\mu_{BUF}E_{DC} > t_{SCODA}\mu_{BUF}E_{SCODA} \quad (5)$$

where: $T_{INJ}$ is the length of time that the DC injection field is applied; $E_{DC}$ is the magnitude of the DC injection field; $t_{SCODA}$ is the length of the time interval in one SCODA cycle during which a reverse field is applied between electrodes 33A and 33C, and $E_{SCODA}$ is the magnitude of the SCODA field applied in that interval. In an example embodiment of SCODA, $t_{SCODA}$ is three seconds, or ¼ of the duration of the SCODA cycle.

In embodiments wherein SCODA and the DC injection fields are interleaved in time, once the SCODA field has been applied for an appropriate amount of time it is shut off and the DC injection can be resumed to introduce further charged molecules into the gel. The cycle can be repeated to enhance the concentration of selected molecules at focus 40.

It is also possible to apply the DC injection field in superposition with the SCODA field. In this case, particles P will enter medium 34 and be focused by SCODA at the same time. Focus spot 40 will continue to increase in molecule concentration, as long as more molecules P are available in buffer reservoir 32A, and as long as the DC injection field is at least periodically or sporadically turned on to cause molecules P to be injected into medium 34. When SCODA and DC fields are applied simultaneously, the DC field will cause the location of focus spot 40 to be pushed away from the location that focal spot 40 would have in the absence of the DC injection field.

An estimate of the amount that focal spot 40 is shifted by a DC field can be made using analytic approximations to the SCODA velocity of Equation (3) and the approximation of the drift velocity of the particles in the DC injection field of:

$$|\vec{v}| = \mu_0 E_{DC} \quad (6)$$

Both of these velocities are taken in the horizontal direction. The DC drift will cause the focus to shift to a location where these velocities are equal and opposite. This will occur at:

$$r = 4\frac{\mu_0 E_{DC}}{kEE_q} \quad (7)$$

in other words, the focus location will be based on the applied fields, and on the ratio of $\mu_0/k$ for the molecules. This yields the additional advantage that molecules may be separated according to the parameter $\mu_9/k$. Typically, for DNA, $\mu_0$ decreases with increasing length, while k increases with increasing length. Clearly, longer molecules will tend to focus nearer to the center of medium 34 with both SCODA and DC injection fields applied, and shorter molecules will focus closer to the edge of medium 34. By increasing the DC field, one can push the foci at which smaller molecules collect off the edge of medium 34 to remove such smaller molecules from medium 34. This mechanism can be applied for enriching a focal spot 40 with large DNA and also for separating DNA or other molecules with small $\mu_0/k$ from molecules with large $\mu_0/k$ (ions, possibly proteins fall in this latter category).

In embodiments wherein the SCODA and DC injection fields occur at the same time, it is desirable to start DC injection first for a period sufficient that the condition of Equation (5) is satisfied. The molecules of interest in buffer reservoir 32A will then be sufficiently far from electrode 33A that they will not be driven into electrode 33A by the SCODA field.

An electrically conducting fluid barrier 44, such as a barrier made of gel, may optionally be placed between electrode 33A and sample S to avoid the possibility that particles in sample S will contact electrode 33 by convective mixing or otherwise.

By applying DC electrokinetic injection during SCODA operation, the concentration factor achievable by SCODA can be increased by injecting for longer, rather than or in addition to using a bigger medium 34.

Apparatus 30 comprises a source 48 of sample S that can be introduced into buffer reservoir 32A by way of valve 50 and pump 52. Excess sample S can escape from buffer reservoir 32A by way of overflow 54. Additional particles P can be made available for concentration in focal spot 40 by periodically or continuously operating pump 52 to introduce fresh sample S into buffer reservoir 32A.

Apparatus 30 also includes a source 58 of clean buffer solution B. When a desired amount of particles P have collected at focal spot 40, sample S can be purged from buffer reservoir 32A by switching valve 50 and operating pump 52 to flush buffer reservoir 32A with buffer B. Continued application of the DC injection field after sample S has been removed from buffer reservoir 32A causes those particles P that are not trapped at focal spot 40 by application of the SCODA fields to be washed out of medium 34 into buffer reservoir 32C.

Where SCODA can achieve a spot radius of 200 µm, performing SCODA on a 1 cm by 1 cm gel medium 34 in which particles P are initially evenly distributed (as would be the case, for example, if the sample is cast as part of the gel) provides a concentration factor of 800. Adding a 10 cm long sample reservoir next to the SCODA gel and performing DC injection while SCODA is running can increase the concentration factor to 8,000. Once the sample reservoir is depleted of particles of interest, it can be drained and replenished with more sample and run again. Each run adds to the concentration factor. Concentration factors in excess of 10,000 times have been achieved.

The methods described herein can be used to collect particles of interest from extremely dilute samples. For example, in one experiment, a sample was made up by diluting approximately 10 molecules of DNA having a target sequence into 5 ml of buffer. The resulting solution (in which the DNA had a zeptomolar $\sim 10^{-21}$ M concentration) was subjected to DC injection and SCODA as described herein. A plug of gel was removed at the SCODA focal spot. The plug of gel was subjected to a SYBR green chemistry RT-PCR reaction. The target DNA sequence was identified in the resulting amplified DNA.

Apparatus according to the invention may comprise appropriate pumps and valves to repeatedly draw fresh sample into the buffer sample reservoir, inject until depleted or substantially depleted of molecules (or other particles) of interest, then drain and renew with fresh sample. Such pumps and valves may be operated automatically under control of an automatic controller such as a computer, PLC, hard-wired logic circuit, some combination thereof, or the like.

Figure 4A:
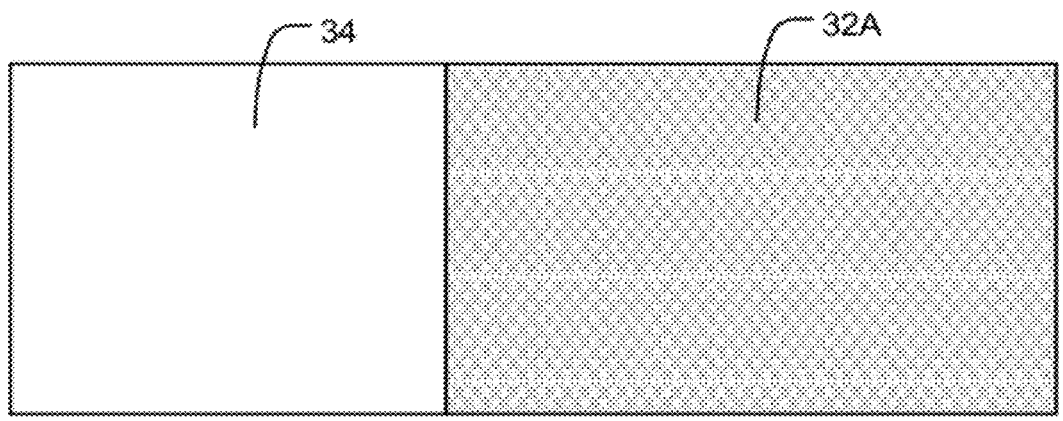
FIGS. 4A through 4D illustrate the operation of a method according to the invention.

In a prototype demonstration of DC electrokinetic injection, a DC injection field was applied until the buffer reservoir was depleted before running the SCODA field. FIGS. 4A to 4D schematically demonstrate this process. Electrodes are not shown in FIGS. 4A to 4D. In FIG. 4A, a sample S is in a buffer reservoir 32A adjoining a SCODA medium (such as a gel) 34. Sample S contains particles of interest.

Figure 4B:
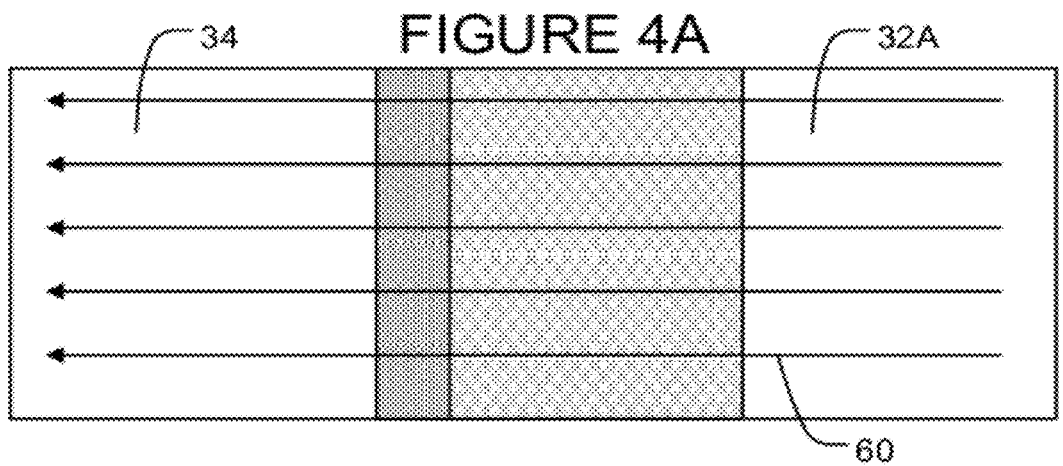
Figure 4C:
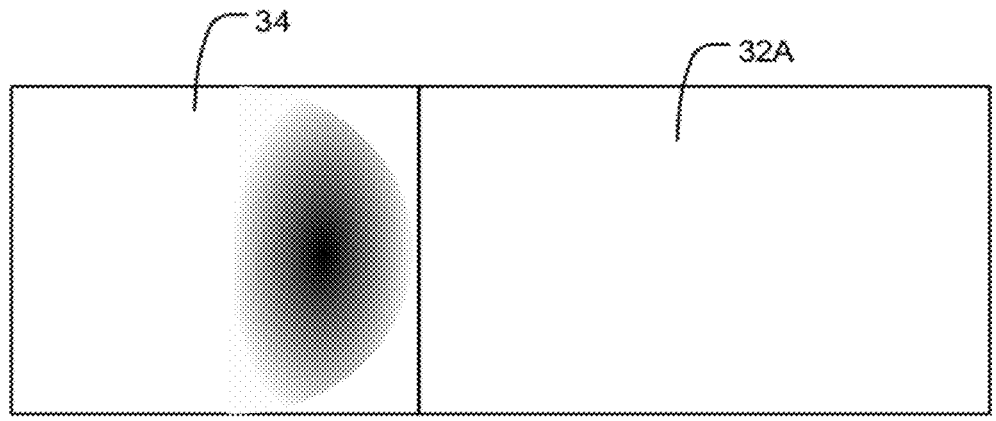
Figure 4D:
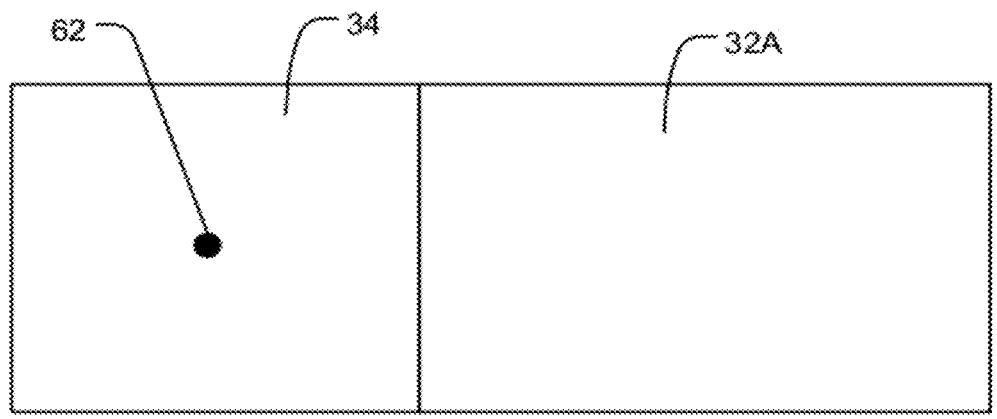

In FIG. 4B, a DC injection field 60 is applied. The DC injection field causes particles to move from reservoir 32A into medium 34. In FIG. 4C, SCODA fields have started to concentrate the particles at a focal spot. In FIG. 4D, continued application of the SCODA fields has caused the particles to be concentrated at a focal spot 62.

Figure 5A:
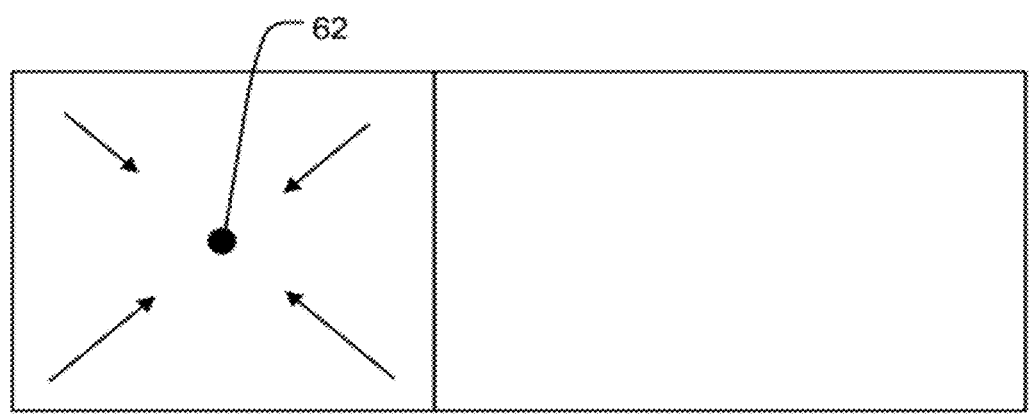
FIGS. 5A and 5B illustrate the deflection of SCODA focused DNA spots by application of a DC field.
Figure 5B:
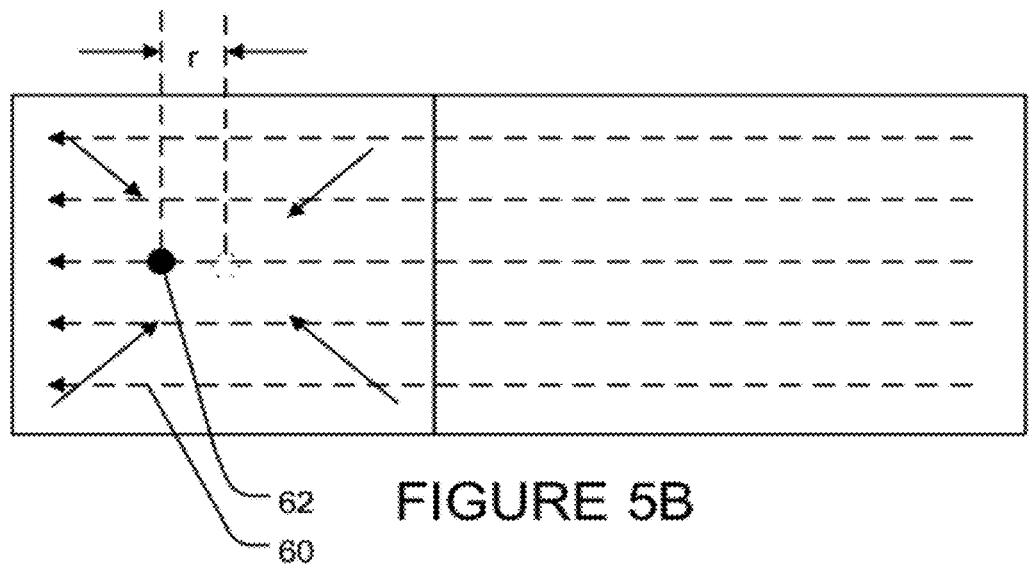

In a separate experiment, SCODA was run while the DC field was applied to observe the deflection of the focal spot. FIG. 5A illustrates the location of focal spot 62 when SCODA fields are applied in the absence of an injection field. FIG. 5B shows how focal spot 62 is displaced by a distance r when a DC injection field 60 is superposed on the SCODA field.

Sometimes the particles that are concentrated in a focal spot are of different species. The methods may optionally include a step to separate the species that have collected at a focal spot. The separation may comprise a one-dimensional separation. Methods that may be used to separate the species at a focal spot include electrophoresis.

In some embodiments, separation is performed by applying a DC field that tends to move particles from the focal spot in one direction and applying an alternating field having a magnitude that is significantly greater in one polarity than the other but an average value that integrates to approximately zero (a ZIFE field). The alternating field is arranged so that it tends to move the particles in the opposite direction to the DC field.

Under the influence of a DC field, particles move at velocities determined primarily by the value of $\mu_0$. Under the influence of the ZIFE field, the particles move at net drift velocities determined primarily by the value of k.

For different species of particle, one or the other of the two fields will dominate. Depending upon which of the fields dominates, the particles will move away from the focal spot in one direction or the other. Which of the fields dominates for a particular species will depend upon the value of $k/\mu_0$ for that species. The result of separation is a smear or a series of spots spread out along a line as indicated in FIG. 6C. For a species having a given value of $k/\mu_0$ it is possible to choose fields so that the effect of the DC and alternating fields on the species is balanced. In this case, the species will stay at the focal spot.

In general, for DNA, k increases with molecular weight and $\mu_0$ decreases with molecular weight. Therefore, separating species of DNA based upon the ratio $k/\mu_0$ generally corresponds to separating the DNA species by molecular weight.

Though some drift of desired bands will likely occur, careful mapping of molecular weight to DC/ZIFE field ratios may allow for removal of DNA fragments outside a relatively tight molecular weight range by selecting conditions which will result in molecules of a particular weight staying at the focal spot and extracting the center of the focal spot after the linear spreading process has been proceeding for sufficient time to move other species away from the focal spot. If enrichment of high molecular weight DNA is desired, the fields are chosen such that the species that is at equilibrium (i.e. does not move away from the focal spot) has a large value of $k/\mu_0$ so that DNA having the highest molecular weight lags near the focal spot. Though this may appear similar to DC electrophoresis, it should be noted that, since the average velocity of the desired band is near zero, substantial separation can be achieved in a short distance, though possibly over a long time.

Figure 6A:
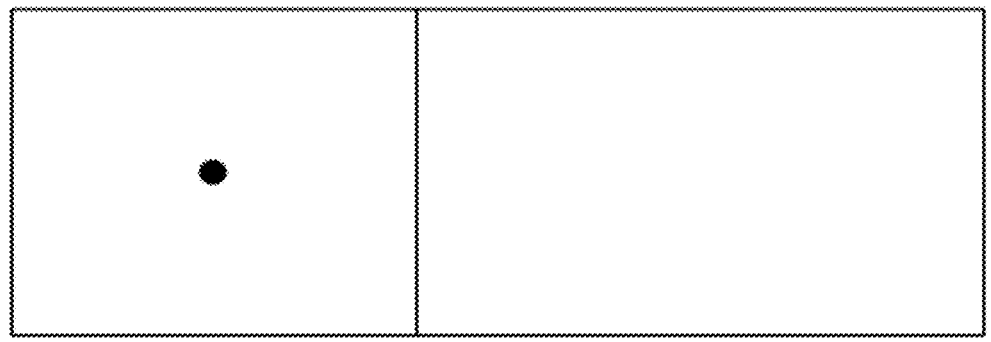
FIGS. 6A, 6B and 6C illustrate separation of particles that have been concentrated at a focal spot by a one-dimensional separation technique.
Figure 6B:
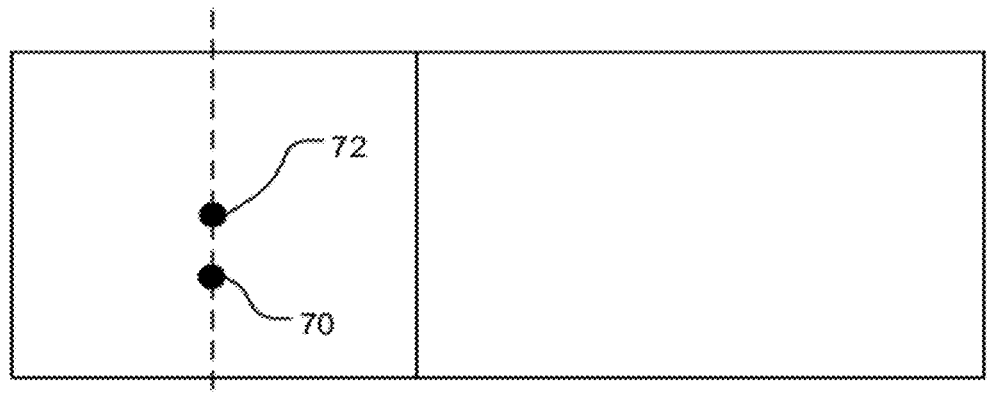
Figure 6C:
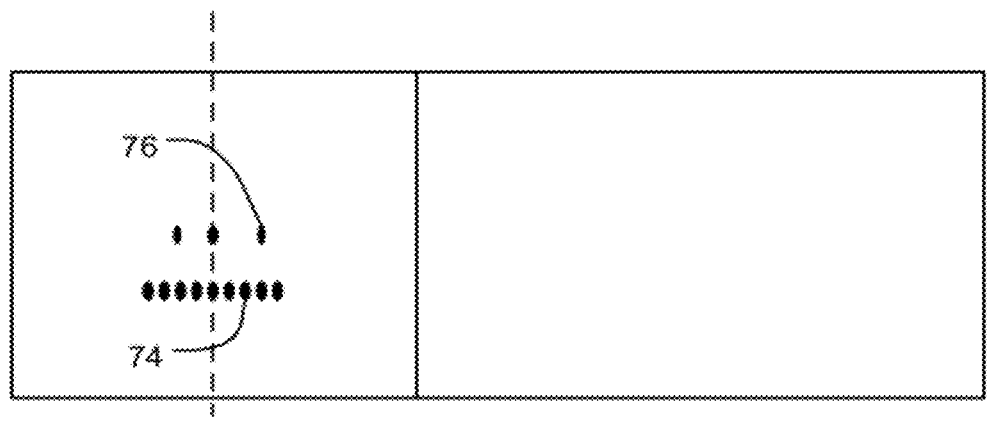

As shown in FIGS. 6B and 6C a spot 70 of a marker, such as a DNA ladder, may be applied adjacent a focal spot 72. After separation, species in the focal spot and ladder are separated. During the separation step, the ladder separates into spots 74 containing species having known lengths or other characteristics. These spots can be correlated to spots 76 resulting from the separation of species in focal spot 72 to identify characteristics of the species in focal spot 72.

In some embodiments, the locations of one or more specific marker spots 74 are monitored. The position of a marker spot can be used to control the ratio of DC/ZIFE fields, to stabilize the location of a band of interest. The controller may control a magnitude of one of the DC and ZIFE fields or may control magnitudes of both the DC and ZIFE fields. In one embodiment, a marker spot 74 contains particles which have the same properties as particles being screened for and the controller uses negative-feedback control to maintain the marker spot 74 stationary. The position of a marker spot 74 may be monitored by a machine vision system, for example.

As will be apparent to those skilled in the art in light of the foregoing disclosure, many alterations and modifications are possible in the practice of this invention without departing from the spirit or scope thereof. For example:

An asymmetrical alternating electric field could be used to drive particles of interest into a medium if the field is selected so that the particles of interest are driven farther into the medium on portions of the cycle which tend to move particles into the medium than the particles of interest are moved back toward the sample on portions of the cycle during which the alternating particle injecting field causes the particles to move back toward the sample.

A membrane or other barrier that is electrically conducting but blocks the passage of the particles may be disposed between the electrode in electrical contact with the sample (e.g. electrode 13C) and the medium. The sample may be introduced between the barrier and the medium. This prevents the particles of interest in the sample from contacting the electrode.

An electrode could be provided within the medium and used for the purpose of injecting particles of interest into the medium. The electrode could be disconnected or removed during SCODA (at least before particles of interest could reach the electrode). Such an electrode could, for example, be located in a well located in a central region of the medium. Such an electrode could provide a radial electric field having a polarity to inject particles-of-interest into the medium. With this arrangement, particles could be injected into the medium from any or all sides of the medium.

Sample could be introduced out of the plane of a sheet-like medium. For example, a layer of fluid containing a sample could be placed on a layer of gel. Particles (such as molecules of interest) could be driven from the fluid into the gel by applying a particle-injecting electric field having a component normal to the surface of the gel and a polarity appropriate to cause the molecules to enter the gel. The electrode(s) used to apply the particle-injecting field could be removed prior to commencing the application of SCODA fields if the presence of such electrode(s) would undesirably disrupt the SCODA fields. The layer of fluid containing the sample could also be removed after the particles-of-interest have been injected into the medium, if desired.

A fluid sample containing particles of interest could be caused to flow through a passageway bounded at least in part by the medium. A particle-injecting field could be applied to cause particles of interest to enter the medium from the fluid flowing in the passageway. Such an embodiment could be applied, for example, to environmental monitoring.

A reservoir containing a sample does not need to be external to the medium but could comprise a passage or other chamber within the medium. For example, the methods of the invention could be applied to inject particles-of-interest into a medium from a passageway extending partially or entirely within the medium along an edge thereof.

Those skilled in the art will recognize that the technology described herein has a wide range of applications, including applications such as:

Extracting DNA from soil—A device could apply the methods described herein to extract target DNA of interest from soil samples for applications such as forensics, environmental pathogen detection, or metagenomics studies. A soil sample could be resuspended in a buffer/lysis solution and added to a buffer reservoir of apparatus as described herein. DC loading fields could be applied across the buffer reservoir to load the DNA into a separation matrix, then concentration fields applied to concentrate the DNA to a focal spot for extraction. The concentrated DNA could then be added to a quantitative real-time PCR reaction with target-specific probes to detect the absence or presence and amount of target DNA sequences in the sample.

Extracting DNA from large volumes of solution—apparatus having a flow-though pumping system as shown, for example, in FIG. 3 could be used to continually cycle sample through a buffer reservoir, therefore permitting concentration of nucleic acids from an arbitrarily large sample volume. In an alternative embodiment, the apparatus may lack a separate buffer reservoir for receiving sample. Injection electrodes could be positioned in such a way to load particles of interest directly into a SCODA medium from a large volume of solution. For example, apparatus could be placed in a water reservoir. An electrode could be provided to load DNA from the reservoir into a SCODA medium. Such apparatus could be used to test water reservoirs for contamination such as *E. coli*. In some cases, real-time detection could be built into a single system to integrate the concentration and detection of target sequences.

Concentrating nucleic acids from airborne pathogens—Air particulate filters, such as those used on airplanes, may be rinsed in solution to release collected airborne pathogens and/or viruses into the solution. The nucleic acids can then be lysed and concentrated. A target-specific detection technique can then be used to rapidly identify targets such as SARS, avian flu, anthrax, or the like.

RNA concentration to determine gene expression—Cellular lysate may be injected and concentrated under conditions which enrich and concentrate RNA for gene expression studies. The concentrated RNA could be transcribed into cDNA by reverse-transcription PCR and analyzed by microarray analysis or SAGE, for example.

While a number of exemplary aspects and embodiments have been discussed above, those of skill in the art will recognize that certain modifications, permutations, additions and sub-combinations thereof are useful. It is intended that the following appended claims and claims hereafter introduced are interpreted to include all such modifications, permutations, additions and sub-combinations as are within their true spirit and scope.

What is claimed is:

1. A method for concentrating target particles, the method comprising:

providing a liquid sample comprising particles, including the target particles, in a reservoir and introducing the target particles from the reservoir into a thin layer of a medium with which the target particles can reversibly bind by applying a first electric field across a boundary between the reservoir and the medium;

applying a sequence of second electric fields to the medium by applying electrical potentials to three or more non-collinear electrodes spaced apart around a periphery of the medium, the sequence of second electric fields causing the target particles in the medium to converge toward a focus location, wherein at least some of the second electric fields vary spatially in the medium such that, in a first area of the medium on a line between a first one of the electrodes and the focus location, the second electric field is oriented in a vector direction to urge the target particles toward the focus location and a magnitude of the second electric field in the first area of the medium is greater than a magnitude of the second electric field in a second area of the medium on a line between a second one of the electrodes and the focus location wherein:

the first and second areas are equidistant from the focus location; and in the second area the second electric field has a vector direction non-parallel to a vector direction of the second electric field in the first area such that target particles in the second area are urged away from the focus location by the second electric field in the second area.

2. A method according to claim 1 comprising:

introducing non-target particles from the reservoir into the medium;

moving the non-target particles through and out of the medium by applying a bias electric field while keeping the target particles within the medium by intermittent or continuous application of the second electric fields.

3. A method according to claim 1 wherein the target particles comprise a nucleic acid comprising a target sequence and the medium comprises an oligonucleotide complementary to the target sequence.

4. A method according to claim 3 comprising introducing one or more of: a protease, a nuclease inhibitor, RNAase, and a denaturing agent into a sample containing the targeted nucleic acid prior to introducing the targeted nucleic acid into the medium.

5. A method according to claim 3 wherein a binding of the target particles to the medium has a strength that is temperature-dependent.

6. A method according to claim 3 wherein the medium comprises a polymer gel and the oligonucleotide is covalently bonded to the polymer gel.

7. A method according to claim 6 wherein the polymer gel comprises an agarose gel.

8. A method according to claim 6 wherein the polymer gel comprises an acrylamide gel.

9. A method according to claim 1 wherein applying the electrical potentials to the electrodes comprises applying a first electrical potential to one of the electrodes such that potential differences between the first electrical potential and the electrical potentials of the rest of the electrodes are greater than potential differences between the electrical potentials of any two of the rest of the electrodes.

10. A method according to claim 9 wherein applying the sequence of second electric fields comprises rotating the electrical potentials such that the first electrical potential is applied to a different one of the electrodes.

11. A method according to claim 1 comprising applying the first electric field simultaneously with the second electric fields.

12. A method according to claim 1 comprising applying the first and second electric fields in alternation.

13. A method according to claim 1 wherein applying the sequence of second electric fields overlaps in time with applying the first electric field.

14. A method according to claim 1 comprising causing localized heating in the medium by application of the second electric fields.

15. A method according to claim 14 comprising cooling a substrate on which the medium is supported.

16. A method according to claim 1 comprising altering a mobility of the target particles in the medium by altering a temperature of the medium in time with the application of the second electric fields.

17. A method according to claim 1 wherein the focus location is free of electrodes.

18. A method according to claim 1 comprising allowing the target particles to bind and unbind to binding sites in the medium.

19. A method according to claim 15 wherein a characteristic time for the target particles to unbind from the medium follows an Arrhenius relationship.

20. A method according to claim 1 comprising replenishing the reservoir with additional particles, including additional target particles, applying the first field to move at least some of the additional target particles from the reservoir into the medium; and, when the additional target particles are in the medium, concentrating the additional target particles together with the target particles by applying the sequence of second electric fields wherein the medium comprises a gel.

21. A method according to claim 1 wherein the method comprises changing the liquid in the reservoir.

22. A method according to claim 21 comprising causing the liquid containing the particles to flow through the reservoir.

23. A method according to claim 1 comprising, after moving the target particles from the reservoir into the medium, removing particles from the reservoir and continuing to apply the first field for a period sufficient to substantially remove non-target particles from the medium while keeping the target particles within the medium by intermittent or continuous application of the second electric fields.

24. A method according to claim 20 wherein moving particles from the reservoir comprises flushing the reservoir with a liquid that does not contain non-target particles.

25. A method according to claim 21 wherein the liquid comprises an aqueous buffer solution.

26. A method according to claim 1 wherein each of the electrodes is in electrical contact with the medium by way of an electrically-conductive buffer solution and the method comprises, for one or more of the electrodes, monitoring an electrical potential within the corresponding buffer solution and controlling the electrical potential on the electrode based at least in part on the monitored electrical potential in the buffer solution.

27. A method according to claim 1 wherein providing the particles in the reservoir comprises preparing a cell lysate and introducing the cell lysate into the reservoir.

28. A method according to claim 3 comprising collecting the targeted nucleic acid at the focus location.

29. A method according to claim 8 wherein a well containing a buffer is located at the focus location and the method comprises allowing the target nucleic acid to enter the buffer in the well and then withdrawing the buffer from the well.

30. A method according to claim 1 wherein the target particles comprise molecules of DNA.

31. A method according to claim 30 comprising, after concentrating the target particles, extracting the target particles from the medium.

32. A method according to claim 31 comprising amplifying the target particles by means of the polymerase chain reaction.

* * * * *